United States Patent
Wohland et al.

(10) Patent No.: US 7,021,064 B2
(45) Date of Patent: Apr. 4, 2006

(54) MULTI-COMPARTMENT PACK FOR COOLING OR HEATING OF PRODUCTS

(75) Inventors: William Carl Wohland, Succasunna, NY (US); Rene Thomas Rivero, West New York, NJ (US)

(73) Assignee: Coty, Inc., New York, NY (US)

( * ) Notice: Subject to any disclaimer, the term of this patent is extended or adjusted under 35 U.S.C. 154(b) by 0 days.

(21) Appl. No.: 10/830,260

(22) Filed: Apr. 22, 2004

(65) Prior Publication Data

US 2004/0194472 A1    Oct. 7, 2004

Related U.S. Application Data

(62) Division of application No. 09/880,703, filed on Jun. 13, 2001.

(60) Provisional application No. 60/217,371, filed on Jul. 11, 2000.

(30) Foreign Application Priority Data

Jun. 28, 2000 (DE) .................. 100 32 799

(51) Int. Cl.
*F25D 5/00* (2006.01)
*B65B 63/08* (2006.01)
*F24J 1/00* (2006.01)
*F24J 3/00* (2006.01)

(52) U.S. Cl. ................ 62/4; 62/60; 126/263.07; 126/263.08

(58) Field of Classification Search .......... 62/4, 62/60; 126/263.07, 263.08
See application file for complete search history.

(56) References Cited

U.S. PATENT DOCUMENTS

| | | | |
|---|---|---|---|
| 1,971,364 A | 8/1934 | Zimmer et al. | 126/263.05 |
| 2,675,798 A | 4/1954 | Rosmarin | 126/204 |
| 3,175,558 A | 3/1965 | Caillonette et al. | |
| 3,426,769 A * | 2/1969 | Slewing | 132/290 |
| 3,512,516 A | 5/1970 | Glass et al. | |
| 3,722,752 A * | 3/1973 | Kenkare et al. | 222/145.1 |
| 3,804,077 A | 4/1974 | Williams | |
| 3,913,559 A | 10/1975 | Dandliker | 126/263 |
| 4,338,098 A | 7/1982 | Yamaji | |
| 4,462,224 A | 7/1984 | Dunshee et al. | 62/530 |
| 4,522,190 A | 6/1985 | Kuhn et al. | 126/263 |
| 4,723,974 A | 2/1988 | Ammerman | |
| 5,240,415 A * | 8/1993 | Haynie | 433/216 |
| 5,263,991 A | 11/1993 | Wiley et al. | |
| 5,431,022 A | 7/1995 | Abe | 62/4 |
| 5,492,219 A | 2/1996 | Stupar | |
| 5,520,202 A * | 5/1996 | Arbree | 132/294 |
| 5,542,418 A | 8/1996 | James | 126/263.06 |
| 5,611,329 A | 3/1997 | Lamensdorf | 126/263.07 |
| 5,967,308 A * | 10/1999 | Bowen | 206/219 |
| 6,289,889 B1 * | 9/2001 | Bell et al. | 126/263.07 |

FOREIGN PATENT DOCUMENTS

DE    2454482 A    5/1976
DE    4292666      8/1992

(Continued)

*Primary Examiner*—William C. Doerrler
(74) *Attorney, Agent, or Firm*—Schwegman, Lundberg, Woessner & Kluth, P.A.

(57) ABSTRACT

The present invention relates to a mujlti-compartment pack for colling or heating products. The pack includes a first compartment with a solid matter or a liquid and a second compartment with a liquid wherein the first and second compartment are separated by a removable wall.

6 Claims, 2 Drawing Sheets

FOREIGN PATENT DOCUMENTS

| | | |
|---|---|---|
| EP | 0180375 | 5/1986 |
| EP | 0454912 A1 | 11/1991 |
| WO | WO-87/00409 | 1/1987 |
| WO | WO-91/10102 | 7/1991 |
| WO | WO-94/05136 | 3/1994 |
| WO | WO-00/43286 | 7/2000 |
| WO | WO-00/64301 | 11/2000 |
| WO | WO-01/04548 | 1/2001 |

\* cited by examiner

MULTI-COMPARTMENT PACK FOR COOLING OR HEATING OF PRODUCTS

This application is a divisional of U.S. patent application Ser. No. 09/880,703, filed Jun. 13, 2001, which claims priority to U.S. Provisional Application Ser. No. 60/217,371, filed Jul. 11, 2000, entitled "MULTI-COMPARTMENT PACK FOR COOLING OR HEATING OF PRODUCTS". This application also claims priority to German Patent Application No. 100 32 799.0, filed Jun. 28, 2000.

FIELD OF THE INVENTION

The present invention relates to a multi-compartment pack for cooling or heating of products, in particular cosmetic or pharmaceutical products.

BACKGROUND

Pack variants for heating or cooling, especially for use on the human body, have been known for a long time. In most cases, these packs comprise an interior compartment, normally containing water, and an exterior compartment, containing, for example, a salt. When pressure is exerted onto the interior compartment, its wall tears open, whereby the water which gets into contact with the salt causes, depending upon the type of salt, an exothermal or endothermal reaction. For example, EP 454912 describes a cooling pack in which the separated compartments contain an ammonium salt and urea, if necessary, in order to achieve a very good cooling effect.

U.S. Pat. No. 4,049,408 discloses a cooling pack for blood samples in which double-compartment containers containing ammonium nitrate in one compartment and water in the other compartment and being integrated in a wrappable cover are, after bringing together the two reacting components, wrapped around a cylindrical blood sample thus ensuring its cooling.

A hot pack to be applied on the human body is known from U.S. Pat. No. 4,057,047 in which water contained in an interior compartment having a perforation and water-free magnesium sulphate in a tightly sealed exterior compartment are brought into contact with each other. The exothermal reaction is used, for example, to warm up limbs of sportsmen in winter.

It is an objective of the present invention to provide a pack unit comprising several compartments which may be used to quickly and effectively heat or cool a product on the basis of a chemical reaction in the compartments with the pack unit being at the same time simple to handle and to manufacture.

The multi-compartment pack comprises a first compartment containing a solid matter or a liquid and an adjacent second compartment temporarily separated from said first compartment and containing a liquid, wherein, if the temporary separation of said compartments is eliminated, the substances in both compartments get into contact with each other and cause an endothermal or exothermal reaction, said pack being characterized according to the present invention in that at least one wall of the first compartment and one wall of the second compartment form at the same time a permanent whole contact area to a third compartment, which contains a product to cool or to heat; the first compartment and the second compartment are in contact with the third compartment solely via the contact area; the liquid present in both compartments after interrupting the separation at a sealing between the first compartment and the second compartment makes possible an interchange of heat by transfer via the whole contact area to the third compartment; and the third compartment comprises an opening easily to be opened from the outside from which the heated or cooled product can be taken out following the reaction between the substances contained in the first and second compartments.

SUMMARY

In the present invention, it is preferable that the contact area consists of a material inert towards the reaction partners and which has a good heat conductivity. Examples for a heat-conducting material are aluminum foil, that may be coated with a plastic material such as polyethylene, Saran, polypropylene, polyethylene terephthalate, polyester, polyvinyl acetate, polyvinyl chloride; copolymers of that polymers; and mixtures thereof. The polymers alone or as mixtures may also form the contact areas and the non-contact areas.

The contact area may be formed as a corrugated or wafer-like structure in order to achieve a further extension of its surface.

DETAILED DESCRIPTION

For the purpose of the present invention, the term "contact area" is meant to describe the area between each of the two compartments containing the heating or cooling substance and the liquid belonging to it, and the compartment containing the product that is to be heated or cooled. "Whole contact area" is the total area created by the sum of the contact areas of the first and the second compartment to the third compartment.

For the multi-compartment pack according to the present invention, known salts or other substances may be used to cause an endothermal or exothermal reaction. For an exothermal reaction, it is advantageous if the first chamber contains a dry substance being selected among calcium oxide, calcium chloride, zeolite Beta, zeolite faujasite X, zeolite faujasite Y, zeolite ZSM-5, mordenite, and mixtures thereof. Other zeolites of the structural classes A, chabasite, ERI (erionite), MEL (ZSM-11), MTT (ZSM-23), OFF (offretite) may be used as well provided that they are commercially available, aluminium-rich, and thus hydrophile.

Further materials may be used such as magnesium sulfate, sodium acetate, ferric chloride, calcium chloride, magnesium chloride, zinc chloride etc. which should be anhydrous.

For an endothermal reaction, the first compartment may contain a dry substance being selected among ammonium nitrate, urea, potassium chloride, stannic chloride, ammonium bromide, cobalt chloride, and mixtures thereof, all of them should be anhydrous.

The ratio between the agents involved in the reaction to achieve a suitable exothermal or endothermal reaction can be determined by a person skilled in the art. Preferably, this ratio ranges between 1:0.8 and 1.3 with relation to the weight of the reactants being a chemical reaction agent (salt):water. The weight ratio between the reactants and the product to be cooled or heated can also be determined by a person skilled in the art and defines the degree of temperature change within the product itself. The range temperature change to be achieved for the product is 1° C. 60° C.

Thus, it is possible for example in using the exothermal reaction to rise temperature by 15 to 30° C. due to the reaction with water and thus to warm up the contacted cosmetic or pharmaceutical product by 5 to 20° C. after a short waiting time of 0.1 to 3 minutes depending upon the dimensions of the contact area.

Following the contact with water, the reaction temperature can be lowered e.g. by 20 to 40° C., thus cooling down the contacted cosmetic or pharmaceutical product by 5 to 20° C. after a short waiting time of 0.1 to 3 minutes depending upon the dimensions of the contact area.

Preferably, water, particularly deionized water, is used as the liquid reaction component in the second compartment. Impurities in tap water may be detrimental to package stability and may affect reactions.

In a preferred embodiment of the invention all compartments are formed to be flat with the ratio between the respective side wall height of one compartment and its length or width being in the range of 1:20–300 and wherein the contact area between the third compartment and the first compartment or the first and second compartments respectively represents the largest basic area of a compartment.

In order to achieve a contact area as large as possible between the third compartment and the cooling or heating mixture generated by the reaction in the two other compartments, the dimension of the contact area of the third compartment in this embodiment is at least equal to the sum of the basic areas of the two other compartments.

Further, it is preferred in this embodiment that the third compartment contains an amount of liquid or pasty substance ranging between 0.05 and 1.5 g per $cm^2$ of the contact area.

A preferred embodiment of the multi-compartment pack according to the present invention is characterized in that the contact area is at the same time the separating wall between the first and the second compartments on the one hand and the third compartment on the other.

In the embodiment in which all compartments are formed flat, the basic areas of the compartments containing the solid matter and the liquid for heating or cooling are welded or glued to the basic area containing the product to be heated or cooled.

The "basic area" of a compartment is the largest area of the compartment defined by its dimensions.

The walls of the first compartment and the second compartment are rigid or flexible but preferably all walls are flexible.

Another embodiment of the multi-compartment pack in which all compartments are formed flat, is characterized in that a first compartment and a second compartment are arranged on each of the basic and the top area of the third compartment so that these two areas of the third compartments form at the same time contact areas with the two first compartments and the two second compartments.

Another embodiment of the multi-compartment pack in which all compartments are formed flat, is characterized in that the basic area of a third compartment is arranged on the basic areas of the first and the second compartment while an additional third compartment is arranged on the top areas of the first and the second compartment so that the basic and top areas of the first and the second compartment form at the same time contact areas with the two third compartments.

Further, it is preferred that the top areas of all compartments, i.e. those areas facing the outside instead of another compartment, are made of a thermally insulating material in order to enhance the cooling effect towards the contact area. Examples for a heat-insulating material are thin foamed foils, e.g. from polystyrene which are optionally reinforced with other plastics, such as films. While heat-insulating materials may be preferred, the use of thermal conducting materials may be required to facilitate production and/or reduce costs.

A further embodiment of the invention is a multi-compartment pack wherein at least a part of the first compartment and the second compartment is integrated within the third compartment. This embodiment is characterized e.g. by a spherical container from plastic, glass, metal such as aluminum, or aluminum alloys, which contains the material to cool or to heat. Inside the sphere is a cylinder for instance a metallic cylinder due to heat transfer, containing two chambers (compartments) that contains the chemical reactants. The top portion preferably should contain the water. The cylinder also contains a plunger that, when pressed, breaks the seal between the two chambers and mixes the reactants. The exothermic or endothermic reaction generated by the mixing of the reactants can be used to heat or cool the surrounding product contained in the sphere. The sphere will have a breakable seal to dispense the product. Other geometric shapes may be (but not limited to) cone, pyramid, octahedron, dodecahedron, tetrahedron, icosahedron, hexahedron (cube), etc. or irregular forms.

It is preferred in this embodiment with regular geometrical forms if the largest distance of the non-contact areas from the contact areas is in the range of 10 to 20 cm, more preferably 2–10 cm or less than 3 cm.

Compared with the prior art, the present invention has the special advantages in that for the first time it provides a practical and easily-to-manufacture pack unit capable of cooling or heating smaller and larger packages of a product in a rational way without any significant temperature losses and without external effort. Thus, the effectiveness of a product applied onto the skin can be improved significantly.

The multi-compartment pack according to the present invention may for instance be used for cooling cosmetic products which, shortly before their application, are brought into a properly cooled state, such as after sports cooling cologne, cooling cleansing solution/wipes, cooling eye pads, cooling neck pads, cooling foot treatment solutions, cool SPF lotions. They may as well be used to heat up products such as after bath sauna lotion or cream for the face, hands, and/or body, body oils, cosmetic face masks, massage creams, massage oils, shaving cream, shaving gel, etc.

Other multi-compartment packages could be produced of shapes and materials to numerous too quantify. The key aspect of this invention is that

- chemical reactants can be combined as a result of various triggering mechanisms one such being applied physical pressure
- the exothermic/endothermic reaction produced by the physical mixture of the reactants can be used to warm or cool e.g. cosmetic or pharmaceutical products prior to them being dispensed
- the cooling or warming of specific product types, by a portable, small sized packaging system, will provide the consumer with products whose skin feel and/or performance are enhanced by the temperature at which they can now be delivered.

BRIEF DESCRIPTION OF THE FIGURES

The invention will hereinafter be further explained with a view to some examples. In the drawings attached.

With reference to FIGS. 1 to 3, the multi-compartment pack according to the present invention comprises a first compartment 1 containing a solid matter, for example calcium chloride, and an adjacent second compartment 2 containing water. Both compartments are temporarily separated from each other by a sealing 13 arranged between the compartments and able to be broken open for instance by the exertion of pressure. In order to open this sealing 13, it is required to exert a certain pressure, for instance by the fingers, onto the water in compartment 2. When the sealing 13 has been opened or partially opened, the calcium chloride and the water mix with each other which effect may be enhanced by exerting alternating pressure onto both compartments. Within a couple of seconds up to 1 minute, the temperature in both compartments rises by approx. 50° C. if both compartments contain about 5 g water and 5 g $CaCl_2$, respectively.

Figure 1:
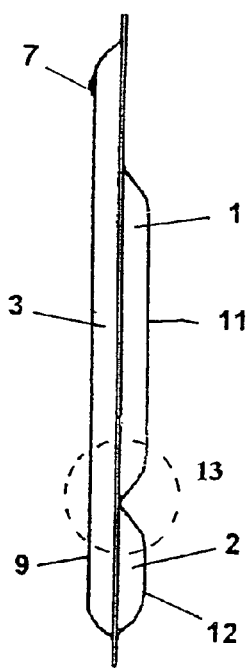
FIG. 1 shows a side view of a multi-compartment pack according to the present invention.
Figure 1A:
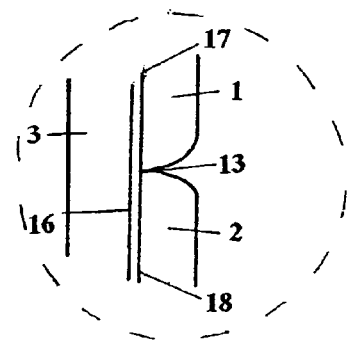
FIG. 1a shows a detail within the circle with a dotted line with closed sealing.
Figure 1B:
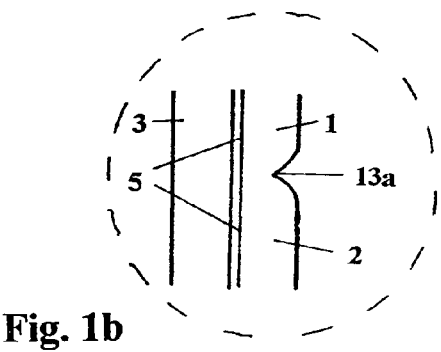
FIG. 1b shows a detail within the circle with a dotted line with closed sealing.
Figure 2:
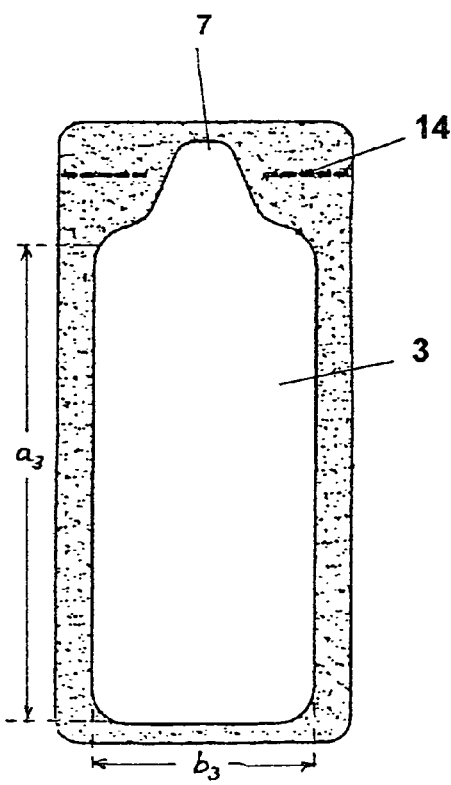
FIG. 2 a planar view of the top area of the third compartment.
Figure 3:
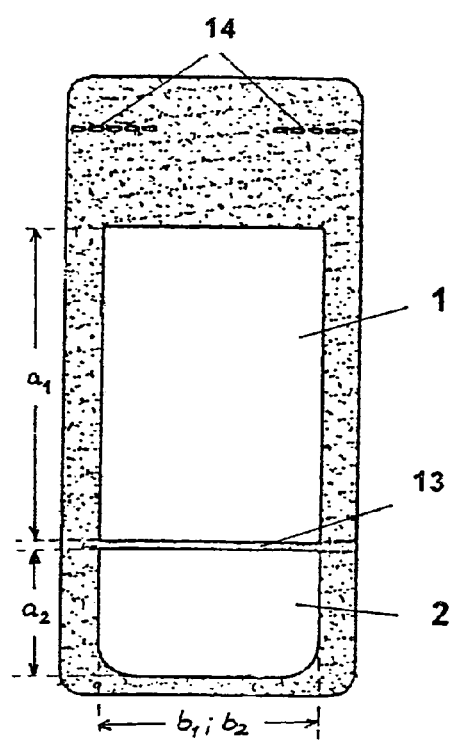
FIG. 3 a planar view of the top areas of the first and the second compartment.

With reference to the embodiment according to FIGS. 1–3 on the area opposite to the basic areas of the first and the second compartment, a third compartment 3 is arranged the basic area of which specified by length a and width b is at least equal to the sum of the basic areas of the two compartments 1 and 2 while the aforementioned basic areas are in contact with each other and form a common contact area.

All compartments in that embodiment are formed flatly, i.e. having a ratio between the respective side wall height (h) of a compartment to its length (a) or width (b) each ranging between 1:20–300, for instance a ratio of 1:100 or 1:50, i.e. at a given side wall height of 2 mm, the compartment may have a length of 200 mm and a width of, for example, 100 mm. Here, the contact area of the third compartment 3 with the first compartment 1 or the first and the second compartments 1, 2 represents the respectively largest basic area of a compartment.

The third compartment is provided with an opening 7 easily to be opened from the outside, from which the heated (or cooled) product can be taken out following the reaction of the substances contained in the first and the second compartments and optionally a short waiting time of 20 seconds to 3 minutes. The opening can be achieved along a provided tear-open breaking line 14 at which part of the compartment wall is broken open.

The basic area of the compartments with which these form the contact area may be made of a material other than that of the top areas of the compartments facing outward. It is preferred that the basic areas are made of a heat-conducting material while the top areas facing outward (e.g. in FIG. 4 the areas 9, 11, and 12) are made of a heat-insulating material.

Figure 4:
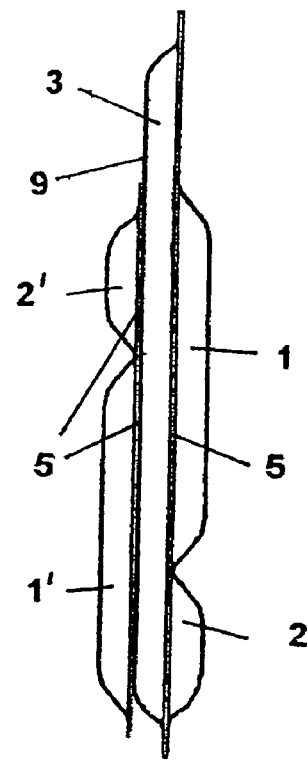
FIG. 4 an embodiment of the present invention comprising two first and two second compartments (side view)

In the embodiment of the present invention illustrated in FIG. 4, a first compartment 1 and a second compartment 2 are arranged on each of the basic area and the top area 9 of the third compartment 3, respectively, i.e. on both sides of compartment 3. Thus, these two areas of the third compartment form at the same time contact areas 5 with the two first compartments 1; 1' and the two second compartments 2; 2'.

Figure 5:
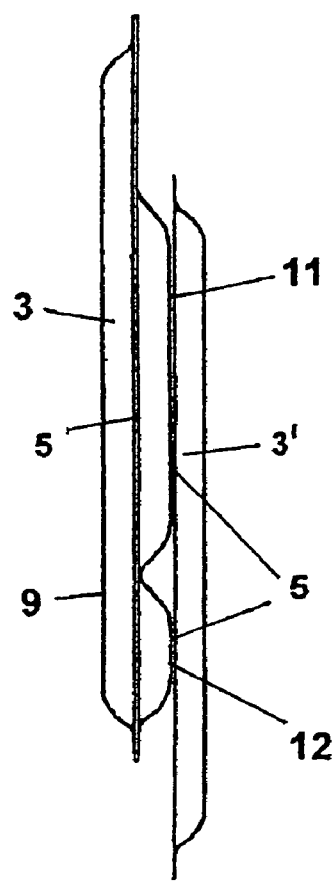
FIG. 5 an embodiment of the present invention comprising two third compartments (side view)

In the embodiment of the present invention illustrated in FIG. 5, a third compartment 3 is arranged with its basic area on the basic areas of the first and the second compartment while an additional third compartment 3' is arranged on the top areas 11 and 12 of the first and the second compartments 1; 2. Thus, the basic and top areas of the first and the second compartments form at the same time contact areas 5 with the two third compartments.

In a further embodiment of the multi-chamber packaging according to the invention are at least a part of the first compartment and the second compartment integrated in the third compartment.

Figure 6:
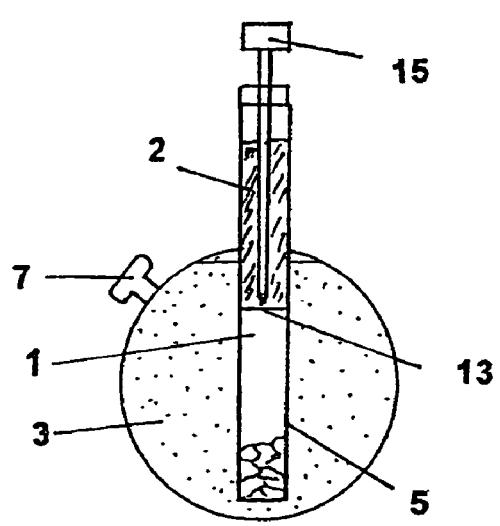
FIG. 6 an embodiment of the present invention with a spherical container for the product (sectional view).

In the embodiment according to FIG. 6, the chambers 1 and 2 are arranged in a cylindrical manner one beneath the other while being surrounded by chamber 3. A plunger 15 for external actuation which projects into chamber 2 is able to break the seal 13 separating chambers 1 and 2 thus causing the contents of the two chambers to become mixed. The product heated or cooled due to the temperature change and exchanged by the contact area 5 is taken out from chamber 3 through the opening 7.

What is claimed is:

1. A kit comprising:
   a multi-compartment pack for cooling cosmetics prior to application to skin, the multi-compartment pack comprising:
   a first compartment;
   a solid or a liquid positioned within the first compartment;
   an adjacent second compartment separated from the first compartment by a removable wall wherein a liquid is positioned within the second compartment, wherein upon breaking or removing the removable wall, the solid or liquid contact each other causing an endothermal reaction, the multi-compartment pack, further comprising:
   a third compartment and a cosmetic enclosed within the third compartment for cooling, the third compartment defined by at least one wall (17) of the first compartment (1) and a wall (18) of the second compartment (2) that form a contact area (5) with a third compartment (3) wherein the cosmetic in the third compartment is cooled, by heat transfer across the contact area, to a temperature effective for applying the cosmetic to skin and cooling the skin; and
   an opening, defined by the third chamber, easily to be opened from the outside, from which the cooled cosmetic can be taken out; and
   one or more applicators for applying the cooled cosmetic to skin.

2. The kit of claim 1 wherein the applicator is one or more of a wipe, pad, sponge, or cloth.

3. A kit comprising:
   a multi-compartment pack for heating cosmetics prior to application to skin, comprising:
   a first compartment;
   a solid or a liquid positioned within the first compartment;
   an adjacent second compartment separated from the first compartment by a removable wall wherein a liquid is positioned within the second compartment, wherein upon breaking or removing the removable wall, the solid or liquid contact each other causing an exothermic reaction, the multi-compartment pack, further comprising:
   a third compartment and a cosmetic enclosed within the third compartment for heating, the third compartment defined by at least one wall (17) of the first compartment (1) and a wall (18) of the second compartment (2) that form a contact area (5) with a third compartment (3) wherein the cosmetic in the third compartment is heated by heat transfer across the contact area to a temperature effective for applying the cosmetic to skin and warming the skin; and
   an opening, defined by the third chamber, easily to be opened from the outside, from which the heated cosmetic can be taken out; and one or more applicators for applying the heated cosmetic to skin.

4. The kit of claim 1 wherein the applicator is one or more of a wipe, pad, sponge, or cloth.

5. A method for cooling a cosmetic prior to application to skin, comprising:

providing a multicompartment container, comprising a first compartment;

a solid or a liquid positioned within the first compartment;

an adjacent second compartment separated from the first compartment by a removable wall wherein a liquid is positioned within the second compartment, wherein upon breaking or removing the removable wall, the solid or liquid contact each other causing an endothermic reaction, the multi-compartment pack, further comprising:

a third compartment containing a cosmetic for cooling, defined by at least one wall (17) of the first compartment (1) and a wall (18) of the second compartment (2) that form a contact area (5) with a third compartment (3) wherein the cosmetic in the third compartment is cooled by heat transfer across the contact area to a temperature effective for applying the cosmetic to skin and cooling the skin; and an opening, defined by the third chamber, easily to be opened from the outside, from which the cooled cosmetic is removed;

breaking the wall separating the first compartment from the second compartment so that the solid or liquid in the first and second compartments mix and cool due to an endothermic reaction;

cooling the cosmetic due to heat transfer from the third compartment to the first and second compartment space; and applying the cooled cosmetic to skin with an applicator.

6. A multi-compartment pack for heating cosmetics prior to application to skin, comprising:

a first compartment;

a solid or a liquid positioned within the first compartment;

an adjacent second compartment separated from the first compartment by a removable wall wherein a liquid is positioned within the second compartment, wherein upon breaking or removing the removable wall, the solid or liquid contact each other causing an exothermic reaction, the multi-compartment pack, further comprising:

a third compartment containing a cosmetic for heating, defined by at least one wall (17) of the first compartment (1) and a wall (18) of the second compartment (2) that form a contact area (5) with the third compartment (3) wherein the cosmetic in the third compartment is heated by heat transfer across the contact area to a temperature effective for applying the cosmetic to skin and heating the skin; and an opening, defined by the third chamber, easily to be opened from the outside, from which the heated cosmetic wherein the third compartment is sized and shaped to enable transfer of the cosmetic to skin; and a third compartment containing a cosmetic for heating, defined by at least one wall (17) of the first compartment (1) and a wall (18) of the second compartment (2) that a contact area (5) with the third compartment (3) wherein the cosmetic in the third compartment is heated by heat transfer across the contact area to a temperature effective for applying the cosmetic to skin and heating the skin; and an opening, defined by the third chamber, easily to be opened from the outside, from which the heated cosmetic can be taken out.

* * * * *

UNITED STATES PATENT AND TRADEMARK OFFICE
CERTIFICATE OF CORRECTION

PATENT NO. : 7,021,064 B2
APPLICATION NO. : 10/830260
DATED : April 4, 2006
INVENTOR(S) : Wohland et al.

It is certified that error appears in the above-identified patent and that said Letters Patent is hereby corrected as shown below:

On the Title page, in field (57), under "Abstract", in column 2, line 1, delete "mujlti" and insert -- multi --, therefor.

On the Title page, in field (57), under "Abstract", in column 2, line 2, delete "colling" and insert -- cooling --, therefor.

In column 7, line 7, in Claim 5, delete "multicompartment" and insert -- multi-compartment --, therefor.

Signed and Sealed this

First Day of August, 2006

JON W. DUDAS
*Director of the United States Patent and Trademark Office*